(12) United States Patent
Blackford

(10) Patent No.: US 8,197,867 B1
(45) Date of Patent: Jun. 12, 2012

(54) DIETARY SUPPLEMENT SYSTEM

(76) Inventor: Richard Blackford, Venice, FL (US)

( * ) Notice: Subject to any disclaimer, the term of this patent is extended or adjusted under 35 U.S.C. 154(b) by 749 days.

(21) Appl. No.: 12/069,127

(22) Filed: Feb. 7, 2008

(51) Int. Cl.
*A61K 36/82* (2006.01)
*A61K 31/34* (2006.01)
*A61K 36/906* (2006.01)
*A61K 36/48* (2006.01)
*A61K 36/00* (2006.01)
*A61K 8/58* (2006.01)

(52) U.S. Cl. ........ 424/729; 424/756; 424/776; 424/779; 424/774; 424/67; 424/757; 514/474

(58) Field of Classification Search .................. None
See application file for complete search history.

(56) References Cited

U.S. PATENT DOCUMENTS

2006/0204599 A1* 9/2006 Wheat ........................... 424/757
2008/0171085 A1* 7/2008 Elnekave et al. ............. 424/465

* cited by examiner

*Primary Examiner* — Patricia Leith
*Assistant Examiner* — Catheryne Chen

(57) ABSTRACT

Of three layers, the first layer in a rapid release composition of a plurality of thermogenic constituents is about 40 percent by weight of the system plus or minus 10 percent. The second layer in a delayed release composition of energy and thyroid stimulating constituents is about 40 percent by weight of the system plus or minus 10 percent. The third layer in a sustained release composition of fat binding and appetite suppressing constituents is 20 percent by weight of the system plus or minus 10 percent.

1 Claim, 1 Drawing Sheet

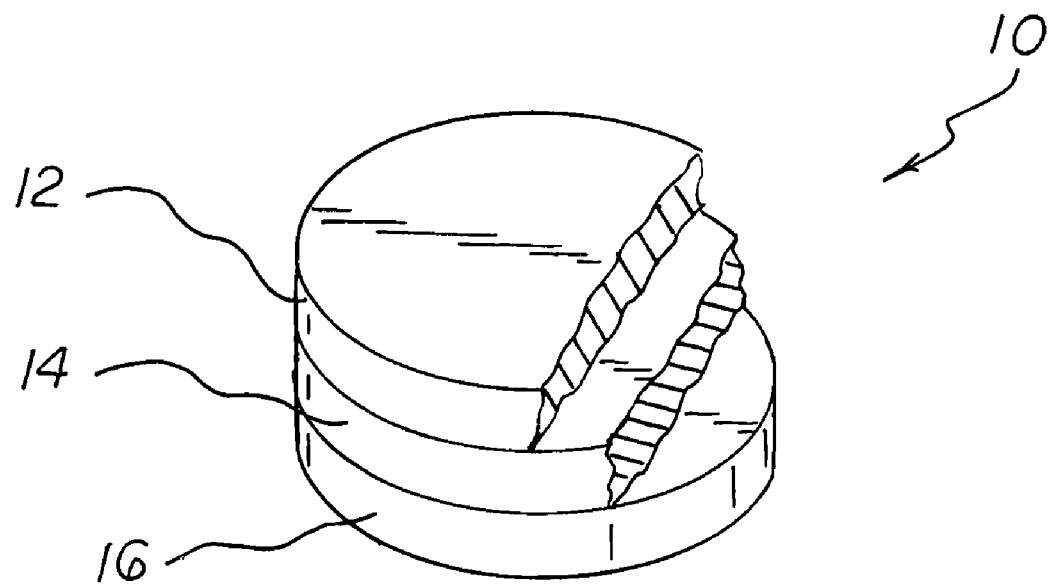

DIETARY SUPPLEMENT SYSTEM

BACKGROUND OF THE INVENTION

1. Field of the Invention

The present invention relates to a dietary supplement system and more particularly pertains to providing rapid thermogenic properties, delayed energy and thyroid stimulating properties and sustained fat binding and appetite suppression properties.

2. Description of the Prior Art

The use of dietary supplements is known in the prior art. More specifically, dietary supplements previously devised and utilized for the purpose of stimulating the body's burning of fat and appetite suppression are known to consist basically of familiar, expected, and obvious structural configurations, notwithstanding the myriad of designs encompassed by the crowded prior art which has been developed for the fulfillment of countless objectives and requirements.

While formulations known in the prior art fulfill their respective, particular objectives and requirements, they do not describe a dietary supplement system that allows providing rapid thermogenic properties, delayed energy and thyroid stimulating properties and sustained fat binding and appetite suppression properties.

In this respect, the dietary supplement system according to the present invention substantially departs from the conventional concepts and designs of the prior art, and in doing so provides a formulation primarily developed for the purpose of providing rapid thermogenic properties, delayed energy and thyroid stimulating properties and sustained fat binding and appetite suppression properties.

Therefore, it can be appreciated that there exists a continuing need for a new and improved dietary supplement system which can be used for providing rapid thermogenic properties, delayed energy and thyroid stimulating properties and sustained fat binding and appetite suppression properties. In this regard, the present invention substantially fulfills this need.

SUMMARY OF THE INVENTION

In view of the foregoing disadvantages inherent in the known types of dietary supplements now present in the prior art, the present invention provides an improved dietary supplement system. As such, the general purpose of the present invention, which will be described subsequently in greater detail, is to provide a new and improved dietary supplement system and method which has all the advantages of the prior art and none of the disadvantages.

To attain this, the present invention essentially comprises a dietary supplement providing a thermogenic first layer (400 mg) in a rapid release composition of constituents including 37.5 percent acaci arigidula extract (150 mg), 6.25 percent ephedra (25 mg), 10 percent theobroma cocao extract 60% (40 mg), 25 percent kola nut extract 50% (100 mg), 21.25 percent citrus aurantium extract 30% (85 mg). The first layer is 40 percent by weight of the system plus or minus 10 percent. The constituents of the first layer are percentages by weight plus or minus 10 percent.

Next provided is an energy and thyroid stimulating second layer (400 mg) in a delayed release composition of constituents including green tea extract, guggulsterones, bladderwrack, bee pollen, ginger root, gotu kola, siberian ginseng, white willow bark, royal jelly, L-carnitine, licorice root, dandelion root, nettle leaf, vitamin E, vitamin C, magnesium, zinc and chromium picolinate. The second layer is 40 percent by weight of the system plus or minus 10 percent. The constituents of the second layer are in substantially equal percentages by weight plus or minus 10 percent.

Lastly provided is a fat binding and appetite suppressing third layer (200 mg) in a sustained release composition of constituents including cassia nomame extract, hoodia gordonii extract, garcinia cambogia extract, and white kidney bean extract. The third layer is 20 percent by weight of the system plus or minus 10 percent. The constituents of the third layer are in substantially equal percentages by weight plus or minus 10 percent.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved dietary supplement system which has all of the advantages of the prior art dietary supplements and none of the disadvantages.

It is another object of the present invention to provide a new and improved dietary supplement system which may be easily and efficiently manufactured and marketed.

It is further object of the present invention to provide a new and improved dietary supplement system which is of durable and reliable constructions.

An even further object of the present invention is to provide a new and improved dietary supplement system which is susceptible of a low cost of manufacture with regard to both materials and labor, and which accordingly is then susceptible of low prices of sale to the consuming public, thereby making such dietary supplement system economically available to the buying public.

Even still another object of the present invention is to provide a dietary supplement system for providing rapid thermogenic properties, delayed energy and thyroid stimulating properties and sustained fat binding and appetite suppression properties.

Lastly, it is an object of the present invention to provide a new and improved dietary supplement in which the first layer in a rapid release composition of a plurality of thermogenic constituents is about 40 percent by weight of the system plus or minus 10 percent; the second layer in a delayed release composition of energy and thyroid stimulating constituents is about 40 percent by weight of the system plus or minus 10 percent; and the third layer in a sustained release composition of fat binding and appetite suppressing constituents is 20 percent by weight of the system plus or minus 10 percent.

These together with other objects of the invention, along with the various features of novelty which characterize the invention, are pointed out with particularity in the claims annexed to and forming a part of this disclosure.

For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective illustration, with parts broken away to show internal constructions, of a dietary supplement system constructed in accordance with the principles of the present invention.

DESCRIPTION OF THE PREFERRED EMBODIMENT

With reference now to the drawing, the preferred embodiment of the new and improved dietary supplement system embodying the principles and concepts of the present invention and generally designated by the reference numeral 10 will be described.

The present invention, the dietary supplement system 10 is comprised of a plurality of components. Such components in their broadest context include a first layer in a rapid release composition, a second layer in a delayed release composition, and a third layer in a sustained release composition. Such components are individually configured and correlated with respect to each other so as to attain the desired objective.

The dietary supplement system 10 (1,000 mg) is for providing rapid thermogenic properties, delayed energy and thyroid stimulating properties and sustained fat binding and appetite suppression properties.

First provided is a thermogenic first layer 14 (400 mg) in a rapid release composition of constituents including 37.5 percent acaci arigidula extract (150 mg), 6.25 percent ephedra (25 mg), 10 percent theobroma cocao extract 60% (40 mg), 25 percent kola nut extract 50% (100 mg), 21.25 percent citrus aurantium extract 30% (85 mg). The first layer is 40 percent by weight of the system plus or minus 10 percent. The constituents of the first layer are percentages by weight plus or minus 10 percent.

Next provided is an energy and thyroid stimulating second layer 16 (400 mg) in a delayed release composition of constituents including green tea extract, guggulsterones, bladderwrack, bee pollen, ginger root, gotu kola, siberian ginseng, white willow bark, royal jelly, L-carnitine, licorice root, dandelion root, nettle leaf, vitamin E, vitamin C, magnesium, zinc and chromium picolinate. The second layer is 40 percent by weight of the system plus or minus 10 percent. The constituents of the second layer are in substantially equal percentages by weight plus or minus 10 percent.

Lastly provided is a fat binding and appetite suppressing third layer 18 (200 mg) in a sustained release composition of constituents including cassia nomame extract, hoodia gordonii extract, garcinia cambogia extract, and white kidney bean extract. The third layer is 20 percent by weight of the system plus or minus 10 percent. The constituents of the third layer are in substantially equal percentages by weight plus or minus 10 percent.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A dietary supplement system consisting of:
    a first layer in a first release composition of a plurality of thermogenic constituents, the first release composition having a first release time, the first layer being 40 percent by weight of the system plus or minus 10 percent;
    a second layer in a second release composition of energy and thyroid stimulating constituents, the second release composition having a second release time greater than the first release time, the second layer being 40 percent by weight of the system plus or minus 10 percent; and
    a third layer in a third release composition of fat binding and appetite suppressing constituents, the third release composition having a third release time greater than the first and second release times, the third layer being 20 percent by weight of the system plus or minus 10 percent
    wherein the thermogenic constituents are chosen from percent Acacia rigidula extract, ephedra, theobroma cocao extract 60%, kola nut extract 50%, citrus aurantium extract 30%;
    wherein the energy and thyroid stimulating constituents are chosen from green tea extract, guggulsterones, bladderwrack, bee pollen, ginger root, gotu kola, siberian ginseng, white willow bark, royal jelly, L-carnitine, licorice root, dandelion root, nettle leaf, vitamin E, vitamin C, magnesium, zinc and chromium picolinate; and
    wherein the fat binding and appetite suppressing constituents are chosen from cassia nomame extract, hoodia gordonii extract, garcinia cambogia extract, and white kidney bean extract.

* * * * *